(12) United States Patent
Anderson et al.

US008124108B2

(10) Patent No.: US 8,124,108 B2
(45) Date of Patent: Feb. 28, 2012

(54) POLYPEPTIDES FOR INDUCING A PROTECTIVE IMMUNE RESPONSE AGAINST STAPHYLOCOCCUS EPIDERMIDIS

(75) Inventors: Annaliesa S. Anderson, Upper Saddle River, NJ (US); Tessie McNeely, Gwynedd Valley, PA (US); James C. Cook, III, North Wales, PA (US); William L. McClements, Doylestown, PA (US); Donna L. Montgomery, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/524,075

(22) PCT Filed: Jan. 18, 2008

(86) PCT No.: PCT/US2008/000647
§ 371 (c)(1),
(2), (4) Date: Jul. 22, 2009

(87) PCT Pub. No.: WO2008/140632
PCT Pub. Date: Nov. 20, 2008

(65) Prior Publication Data
US 2010/0143390 A1 Jun. 10, 2010

Related U.S. Application Data

(60) Provisional application No. 60/897,150, filed on Jan. 24, 2007.

(51) Int. Cl.
*A61K 39/085* (2006.01)
*A61K 39/02* (2006.01)
*C07K 14/31* (2006.01)

(52) U.S. Cl. ............... 424/243.1; 424/184.1; 424/190.1; 530/350

(58) Field of Classification Search ........................ None
See application file for complete search history.

(56) References Cited

U.S. PATENT DOCUMENTS

| 6,380,370 B1 * | 4/2002 | Doucette-Stamm et al. | 536/23.1 |
| 7,060,458 B1 | 6/2006 | Doucette-Stamm et al. | |
| 2004/0147734 A1 | 7/2004 | Doucette-Stamm et al. | |

FOREIGN PATENT DOCUMENTS

| WO | 02/059148 A2 | 8/2002 |
| WO | 03/031588 A2 | 4/2003 |
| WO | 2004/087746 A2 | 10/2004 |
| WO | 2005/009378 A2 | 2/2005 |
| WO | 2005/009379 A2 | 2/2005 |
| WO | 2005/079315 A2 | 9/2005 |
| WO | 2005/086663 A2 | 9/2005 |
| WO | 2005/115113 A2 | 12/2005 |
| WO | 2006/033918 A2 | 3/2006 |
| WO | 2006/078680 A2 | 7/2006 |

OTHER PUBLICATIONS

Geissler 1996 Journal of bacteriology ,178, (1) 284-288.*
Broun et al (Science 282:1315-1317, 1998).*
Seffernick et al., (J. Bacteriol. 183(8): 2405-2410, 2001).*
Witkowski et al (Biochemistry 38:11643-11650, 1999).*
Amorena Beatriz et al. "Use of liposome-immunopotentiated exoplysaccharide as a component of an ovine mastitis staphylococcal vaccine", Vaccine, 1994; 12(3): 243-249.
Gotz, Friedrich, "Staphylococci in colonization and disease: prospective targets for drugs and vaccines", Current Opinion in Microbiology, 2004; 7: 477-487.
Jiang, Ming et al., "Menaquinone Biosynthesis in *Escherichia coli*: Identification of 2-Succinyl-5-enolpyruvyl-6-hydroxy-3-cyclohexene-1-carboxylate as a Novel Intermediate and Re-Evaluation of MenD Activity", Biochemistry, 2007; 46: 10979-10989.
McKenney, David et al., "Vaccine potential of poly-1-6 β-D-N-succinylglucosamine, an immunoprotective surface polysaccharide of *Staphylococcus aureus* and *Staphylococcus epidermidis*", Journal of Biotechnology, 2000; 83: 37-44.
Barouch "Rational design of gene-based vaccines", Journal of Pathology, 2006, vol. 208, pp. 283-289.
Gill et al. "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain", Journal of Bacteriology, 2005, vol. 187, pp. 2426-2438.
Josefsson et al. "Protection against Experimental *Staphylococcus aureus* Arthritis by Vaccination with Clumping Factor A, a Novel Virulence Determinant", The Journal of Infectious Diseases, 2001, vol. 184, pp. 1572-1580.
Joyce, et al. "Isolation, structural characterization, and immunological evaluation of a high-molecular-weight exopolysaccharide from *Staphylococcus aureus*", Carbohydrate Research, 2003, vol. 338, pp. 903-922.
Klein, et al. "Analysis of Aluminum Hydroxyphosphate Vaccine Adjuvants by 27Al MAS NMR", Journal of Pharmaceutical Sciences, 2000, vol. 89, pp. 311-321.
Mamo et al. "Vaccination with *Staphylococcus aureus* fibrinogen binding proteins (FgBPs) reduces colonisation of *S. aureus* in a mouse mastitis model", FEMS Immunology and Medical Microbiology, 1994, vol. 10, pp. 47-54.
Nilsson et al. "Vaccination with a Recombinant Fragment of Collagen Adhesin Provides Protection against *Staphylococcus aureus*—mediated Septic Death", The Journal of Clinical Investigation, 1998, vol. 101, p. 2640-2649.

(Continued)

*Primary Examiner* — Padma Baskar
(74) *Attorney, Agent, or Firm* — Alysia A. Finnegan; Sheldon O. Heber

(57) ABSTRACT

The present invention features polypeptides comprising an amino acid sequence structurally related to SEQ ID NO: 1 and uses of such polypeptides. SEQ ID NO: 1 is a truncated derivative of a full-length *S. epidermidis* polypeptide. The full-length naturally occurring polypeptide is referred to herein as full-length ORF1319e. A His-tagged derivative of SEQ ID NO: 1 was found to produce a protective immune response against *S. epidermidis*.

5 Claims, 3 Drawing Sheets

OTHER PUBLICATIONS

Shinefield, et al. "Use of *Staphylococcus aureus* Conjugate Vaccine in Patients Receiving Hemodialysis", The New England Journal of Medicine, 2002, vol. 346, pp. 491-496.

Vogel "Improving Vaccine Performance with Adjuvants", Clinical Infectious Diseases, 2000, vol. 30, Suppl 3, pp. S266-S270.

Zhang, et al. "Genome-based analysis of virulence genes in a non-biofilm-forming *Staphylococcus epidermidis* strain (ATCC 12228)", Molecular Microbiology, 2003, vol. 49, pp. 1577-1593.

Ziebuhr, et al. "Nosocomial infections by *Staphylococcus epidermidis*: how a commensal bacterium turns into a pathogen", International Journal of Antimicrobial Agents 28S, 2006, vol. 28S, pp. S14-S20.

Gen-Bank Accession No. Q8CPQ5 Oct. 31, 2006.

Gen-Bank Accession No. Q5HQC5 Oct. 31, 2006.

\* cited by examiner

MGHHHHHHSQISRLPLVVLTSDRPHELRSVGAPQAINQVNMFSNYVNFQFDLPIADGSEHTIDTINYQMQIASQY
LYGPHRGPIHFNLPFREPLTPDLDRVDLLTSVTKTLPHYQKSISVDDIKDILQEKNGLIIVGDMQHQAVDQILTY
STIYDLPILADPLSQLRKEKHPNVITTYDLLYRAGLNLEVDYVIRVGKPVISKKLNQWLKKTDAYQIIVQNNDQI
DVFPTPPHISYEISANDFFRSLMEEPLVERKKWLQQWQSLEQQARIEISDYLKHATDEAAYVGSLIQKLTKEDTL
FVGNSMPIRDVDNLLFDSEASVYANRGANGIDGVVSTALGMAAHKNVTLLIGDLSFYHDMNGLLMAKLNELHINI
VLVNNNGGGIFSYLPQKRSATKYFERLFGTPTGLNFEYTALLYDFTFKRFDNLTDFKYAELSKMGSHMYEVITNR
DENLHQHQNLYQKLSEIVNVTL

FIGURE 1

```
MMNHSEALTEQVFSFASELYAYGVREVVISPGSRSTPLALVFEAHPNIKTWIHPDERSAAFFALGLIKGSEKPVA
ILCTSGTAAANYTPAIAESQISRLPLVVLTSDRPHELRSVGAPQAINQVNMFSNYVNFQFDLPIADGSEHTIDTI
NYQMQIASQYLYGPHRGPIHFNLPFREPLTPDLDRVDLLTSVTKTLPHYQKSISVDDIKDILQEKNGLIIVGDMQ
HQAVDQILTYSTIYDLPILADPLSQLRKEKHPNVITTYDLLYRAGLNLEVDYVIRVGKPVISKKLNQWLKKTDAY
QIIVQNNDQIDVFPTPPHISYEISANDFFRSLMEEPLVERKKWLQQWQSLEQQARIEISDYLKHATDEAAYVGSL
IQKLTKEDTLFVGNSMPIRDVDNLLFDSEASVYANRGANGIDGVVSTALGMAAHKNVTLLIGDLSFYHDMNGLLM
AKLNELHINIVLVNNNGGGIFSYLPQKRSATKYFERLFGTPTGLNFEYTALLYDFTFKRFDNLTDFKYAELSKMG
SHMYEVITNRDENLHQHQNLYQKLSEIVNVTL
```

FIGURE 2A

```
ATGATGAATCATAGTGAAGCTTTAACTGAACAAGTATTTTCATTTGCTTCAGAGCTTTATGCTTATGGTGTAAGA
GAAGTAGTAATTAGTCCAGGTTCACGTTCAACACCATTAGCACTTGTTTTCGAAGCACATCCAAATATTAAAACA
TGGATTCACCCTGATGAGCGAAGTGCTGCATTTTTTGCTTTAGGTCTTATTAAAGGTAGCGAAAAACCTGTAGCA
ATTCTTTGTACATCTGGAACAGCCGCTGCGAACTACACACCCGCTATAGCTGAAAGTCAAATTAGTCGTTTGCCT
CTCGTTGTTTTAACGAGCGACAGACCGCATGAACTGCGCAGTGTGGGTGCACCTCAAGCAATCAATCAGGTAAAT
ATGTTTAGTAATTATGTGAACTTTCAATTTGATTTGCCGATTGCTGATGGAAGTGAACATACAATTGATACAATT
AATTATCAAATGCAAATTGCAAGTCAATATTTATATGGACCACACCGAGGACCGATTCATTTTAATTTACCATTT
AGAGAACCACTAACACCAGATTTAGATCGTGTCGATTTATTAACATCTGTAACTAAAACGTTACCTCATTATCAG
AAATCGATTTCGGTAGATGATATAAAAGACATATTACAAGAAAAAAATGGTCTCATCATTGTCGGAGATATGCAA
CACCAAGCTGTTGATCAAATATTAACGTATTCAACTATATATGATCTGCCAATCTTAGCAGATCCCCTTAGTCAG
CTTCGTAAAGAGAAACATCCTAATGTTATAACCACTTATGATTTATTGTATCGAGCAGGATTAAATTTAGAAGTA
GACTATGTCATACGTGTAGGTAAGCCAGTTATTTCTAAAAAATTAAATCAATGGTTGAAGAAAACCGATGCGTAT
CAAATTATTGTGCAGAATAATGATCAAATTGATGTATTTCCGACACCACCTCATATATCTTATGAGATTTCAGCA
AATGATTTTTTCCGTTCATTAATGGAAGAACCACTTGTTGAACGAAAAAAATGGTTACAGCAATGGCAATCACTT
GAACAACAAGCACGCATTGAAATAAGTGATTACTTAAAGCATGCGACAGATGAAGCGGCATATGTAGGGAGTTTA
ATTCAAAAACTTACAAAAGAAGATACATTATTTGTTGGAAATAGTATGCCAATTAGAGATGTCGATAATTTACTG
TTTGATAGTGAGGCATCTGTATACGCTAATCGGGGTGCCAATGGAATAGACGGAGTAGTTTCAACTGCGCTAGGT
ATGGCGGCACATAAGAATGTGACATTGCTTATTGGTGATTTATCTTTTTATCATGACATGAACGGTTTATTAATG
GCCAAATTAAATGAACTTCATATTAACATTGTATTAGTTAATAACAACGGAGGAGGTATCTTTTCATATTTACCT
CAAAAACGATCGGCTACAAAATATTTTGAGCGATTATTTGGAACACCAACAGGCTTAAACTTTGAATATACTGCA
CTGTTATATGATTTTACATTTAAGCGCTTTGATAATTTGACTGACTTTAAATATGCTGAATTATCTAAAATGGGT
TCTCACATGTATGAAGTTATAACCAATAGAGACGAAAATTTGCATCAACACCAAAATTTATATCAGAAATTGAGT
GAGATTGTTAATGTTACATTATAA
```

FIGURE 2B

```
MMNHSEALTEQVFSFASELYAYGVREVVISPGSRSTPLALAFEAHPNIKTWIHPDERSAAFFALGLIKGSEKPVA
ILCTSGTAAANYTPAIAESQISRLPLVVLTSDRPHELRSVGAPQAINQVNMFSNYVNFQFDLPIADGSEHTIDTI
NYQMQIASQYLYGPHRGPIHFNLPFREPLTPDLDRVDLLTSVTKTLPHYQKSISVDDIKDILQEKNGLIIVGDMQ
HQAVDQILTYSTIYDLPILADPLSQLRKEKHPNVITTYDLLYRAGLNLEVDYVIRVGKPVISKKLNQWLKKTDAY
QIIVQNNDQIDVFPTPPHISYEISANDFFRSLMEEPLVERKKWLQQWQSLEQQARIEISDYLKHATDEAAYVGSL
IQKLTKEDTLFVGNSMPIRDVDNLLFDSEASVYANRGANGIDGVVSTALGMAAHKNVILLIGDLSFYHDMNGLLM
AKLNELHINIVLVNNNGGGIFSYLPQKRSATKYFERLFGTPTGLNFEYTALLYDFTFKRFDNLTDFKYAELSKMG
SHMYEVITNRDENLHQHQNLYQKLSEIVNVTL
```

FIGURE 3

SEQUENCE LISTING

```
<160> NUMBER OF SEQ ID NOS: 5
<210> SEQ ID NO 1
<211> LENGTH: 464
<212> TYPE: PRT
<213> ORGANISM: Artificial Sequence
<220> FEATURE:
<223> OTHER INFORMATION: Truncated derivative of the full length
      ORF1319e S. epidermidis polypeptide (SEQ ID NO: 3)

<400> SEQUENCE: 1

Ser Gln Ile Ser Arg Leu Pro Leu Val Val Leu Thr Ser Asp Arg Pro
1               5                   10                  15

His Glu Leu Arg Ser Val Gly Ala Pro Gln Ala Ile Asn Gln Val Asn
            20                  25                  30

Met Phe Ser Asn Tyr Val Asn Phe Gln Phe Asp Leu Pro Ile Ala Asp
        35                  40                  45

Gly Ser Glu His Thr Ile Asp Thr Ile Asn Tyr Gln Met Gln Ile Ala
    50                  55                  60

Ser Gln Tyr Leu Tyr Gly Pro His Arg Gly Pro Ile His Phe Asn Leu
65                  70                  75                  80

Pro Phe Arg Glu Pro Leu Thr Pro Asp Leu Asp Arg Val Asp Leu Leu
                85                  90                  95

Thr Ser Val Thr Lys Thr Leu Pro His Tyr Gln Lys Ser Ile Ser Val
            100                 105                 110

Asp Asp Ile Lys Asp Ile Leu Gln Glu Lys Asn Gly Leu Ile Ile Val
        115                 120                 125

Gly Asp Met Gln His Gln Ala Val Asp Gln Ile Leu Thr Tyr Ser Thr
    130                 135                 140

Ile Tyr Asp Leu Pro Ile Leu Ala Asp Pro Leu Ser Gln Leu Arg Lys
145                 150                 155                 160

Glu Lys His Pro Asn Val Ile Thr Thr Tyr Asp Leu Leu Tyr Arg Ala
```

```
                        165                 170                 175
Gly Leu Asn Leu Glu Val Asp Tyr Val Ile Arg Val Gly Lys Pro Val
            180                 185                 190

Ile Ser Lys Lys Leu Asn Gln Trp Leu Lys Lys Thr Asp Ala Tyr Gln
        195                 200                 205

Ile Ile Val Gln Asn Asn Asp Gln Ile Asp Val Phe Pro Thr Pro Pro
    210                 215                 220

His Ile Ser Tyr Glu Ile Ser Ala Asn Asp Phe Phe Arg Ser Leu Met
225                 230                 235                 240

Glu Glu Pro Leu Val Glu Arg Lys Lys Trp Leu Gln Gln Trp Gln Ser
                245                 250                 255

Leu Glu Gln Gln Ala Arg Ile Glu Ile Ser Asp Tyr Leu Lys His Ala
            260                 265                 270

Thr Asp Glu Ala Ala Tyr Val Gly Ser Leu Ile Gln Lys Leu Thr Lys
        275                 280                 285

Glu Asp Thr Leu Phe Val Gly Asn Ser Met Pro Ile Arg Asp Val Asp
    290                 295                 300

Asn Leu Leu Phe Asp Ser Glu Ala Ser Val Tyr Ala Asn Arg Gly Ala
305                 310                 315                 320

Asn Gly Ile Asp Gly Val Val Ser Thr Ala Leu Gly Met Ala Ala His
                325                 330                 335

Lys Asn Val Thr Leu Leu Ile Gly Asp Leu Ser Phe Tyr His Asp Met
            340                 345                 350

Asn Gly Leu Leu Met Ala Lys Leu Asn Glu Leu His Ile Asn Ile Val
        355                 360                 365

Leu Val Asn Asn Asn Gly Gly Gly Ile Phe Ser Tyr Leu Pro Gln Lys
    370                 375                 380

Arg Ser Ala Thr Lys Tyr Phe Glu Arg Leu Phe Gly Thr Pro Thr Gly
385                 390                 395                 400

Leu Asn Phe Glu Tyr Thr Ala Leu Leu Tyr Asp Phe Thr Phe Lys Arg
                405                 410                 415

Phe Asp Asn Leu Thr Asp Phe Lys Tyr Ala Glu Leu Ser Lys Met Gly
            420                 425                 430

Ser His Met Tyr Glu Val Ile Thr Asn Arg Asp Glu Asn Leu His Gln
        435                 440                 445

His Gln Asn Leu Tyr Gln Lys Leu Ser Glu Ile Val Asn Val Thr Leu
    450                 455                 460

<210> SEQ ID NO 2
<211> LENGTH: 472
<212> TYPE: PRT
<213> ORGANISM: Artificial Sequence
<220> FEATURE:
<223> OTHER INFORMATION: His-Tag derivative of SEQ ID NO: 1

<400> SEQUENCE: 2

Met Gly His His His His His His Ser Gln Ile Ser Arg Leu Pro Leu
1               5                   10                  15

Val Val Leu Thr Ser Asp Arg Pro His Glu Leu Arg Ser Val Gly Ala
            20                  25                  30

Pro Gln Ala Ile Asn Gln Val Asn Met Phe Ser Asn Tyr Val Asn Phe
        35                  40                  45

Gln Phe Asp Leu Pro Ile Ala Asp Gly Ser Glu His Thr Ile Asp Thr
    50                  55                  60

Ile Asn Tyr Gln Met Gln Ile Ala Ser Gln Tyr Leu Tyr Gly Pro His
65                  70                  75                  80
```

```
Arg Gly Pro Ile His Phe Asn Leu Pro Phe Arg Glu Pro Leu Thr Pro
                    85                  90                  95

Asp Leu Asp Arg Val Asp Leu Leu Thr Ser Val Thr Lys Thr Leu Pro
                100                 105                 110

His Tyr Gln Lys Ser Ile Ser Val Asp Asp Ile Lys Asp Ile Leu Gln
            115                 120                 125

Glu Lys Asn Gly Leu Ile Ile Val Gly Asp Met Gln His Gln Ala Val
130                 135                 140

Asp Gln Ile Leu Thr Tyr Ser Thr Ile Tyr Asp Leu Pro Ile Leu Ala
145                 150                 155                 160

Asp Pro Leu Ser Gln Leu Arg Lys Glu Lys His Pro Asn Val Ile Thr
                165                 170                 175

Thr Tyr Asp Leu Leu Tyr Arg Ala Gly Leu Asn Leu Glu Val Asp Tyr
                180                 185                 190

Val Ile Arg Val Gly Lys Pro Val Ile Ser Lys Lys Leu Asn Gln Trp
            195                 200                 205

Leu Lys Lys Thr Asp Ala Tyr Gln Ile Ile Val Gln Asn Asn Asp Gln
210                 215                 220

Ile Asp Val Phe Pro Thr Pro Pro His Ile Ser Tyr Glu Ile Ser Ala
225                 230                 235                 240

Asn Asp Phe Phe Arg Ser Leu Met Glu Glu Pro Leu Val Glu Arg Lys
                245                 250                 255

Lys Trp Leu Gln Gln Trp Gln Ser Leu Glu Gln Gln Ala Arg Ile Glu
                260                 265                 270

Ile Ser Asp Tyr Leu Lys His Ala Thr Asp Glu Ala Ala Tyr Val Gly
            275                 280                 285

Ser Leu Ile Gln Lys Leu Thr Lys Glu Asp Thr Leu Phe Val Gly Asn
290                 295                 300

Ser Met Pro Ile Arg Asp Val Asp Asn Leu Leu Phe Asp Ser Glu Ala
305                 310                 315                 320

Ser Val Tyr Ala Asn Arg Gly Ala Asn Gly Ile Asp Gly Val Val Ser
                325                 330                 335

Thr Ala Leu Gly Met Ala Ala His Lys Asn Val Thr Leu Leu Ile Gly
                340                 345                 350

Asp Leu Ser Phe Tyr His Asp Met Asn Gly Leu Leu Met Ala Lys Leu
            355                 360                 365

Asn Glu Leu His Ile Asn Ile Val Leu Val Asn Asn Asn Gly Gly Gly
370                 375                 380

Ile Phe Ser Tyr Leu Pro Gln Lys Arg Ser Ala Thr Lys Tyr Phe Glu
385                 390                 395                 400

Arg Leu Phe Gly Thr Pro Thr Gly Leu Asn Phe Glu Tyr Thr Ala Leu
                405                 410                 415

Leu Tyr Asp Phe Thr Phe Lys Arg Phe Asp Asn Leu Thr Asp Phe Lys
                420                 425                 430

Tyr Ala Glu Leu Ser Lys Met Gly Ser His Met Tyr Glu Val Ile Thr
            435                 440                 445

Asn Arg Asp Glu Asn Leu His Gln His Gln Asn Leu Tyr Gln Lys Leu
450                 455                 460

Ser Glu Ile Val Asn Val Thr Leu
465                 470

<210> SEQ ID NO 3
<211> LENGTH: 557
<212> TYPE: PRT
```

<213> ORGANISM: Staphylococcus epidermidis

<400> SEQUENCE: 3

```
Met Met Asn His Ser Glu Ala Leu Thr Glu Gln Val Phe Ser Phe Ala
1               5                   10                  15

Ser Glu Leu Tyr Ala Tyr Gly Val Arg Glu Val Val Ile Ser Pro Gly
            20                  25                  30

Ser Arg Ser Thr Pro Leu Ala Leu Val Phe Glu Ala His Pro Asn Ile
        35                  40                  45

Lys Thr Trp Ile His Pro Asp Glu Arg Ser Ala Ala Phe Phe Ala Leu
    50                  55                  60

Gly Leu Ile Lys Gly Ser Glu Lys Pro Val Ala Ile Leu Cys Thr Ser
65                  70                  75                  80

Gly Thr Ala Ala Ala Asn Tyr Thr Pro Ala Ile Ala Glu Ser Gln Ile
                85                  90                  95

Ser Arg Leu Pro Leu Val Val Leu Thr Ser Asp Arg Pro His Glu Leu
            100                 105                 110

Arg Ser Val Gly Ala Pro Gln Ala Ile Asn Gln Val Asn Met Phe Ser
        115                 120                 125

Asn Tyr Val Asn Phe Gln Phe Asp Leu Pro Ile Ala Asp Gly Ser Glu
130                 135                 140

His Thr Ile Asp Thr Ile Asn Tyr Gln Met Gln Ile Ala Ser Gln Tyr
145                 150                 155                 160

Leu Tyr Gly Pro His Arg Gly Pro Ile His Phe Asn Leu Pro Phe Arg
                165                 170                 175

Glu Pro Leu Thr Pro Asp Leu Asp Arg Val Asp Leu Leu Thr Ser Val
            180                 185                 190

Thr Lys Thr Leu Pro His Tyr Gln Lys Ser Ile Ser Val Asp Asp Ile
        195                 200                 205

Lys Asp Ile Leu Gln Glu Lys Asn Gly Leu Ile Ile Val Gly Asp Met
    210                 215                 220

Gln His Gln Ala Val Asp Gln Ile Leu Thr Tyr Ser Thr Ile Tyr Asp
225                 230                 235                 240

Leu Pro Ile Leu Ala Asp Pro Leu Ser Gln Leu Arg Lys Glu Lys His
                245                 250                 255

Pro Asn Val Ile Thr Thr Tyr Asp Leu Leu Tyr Arg Ala Gly Leu Asn
            260                 265                 270

Leu Glu Val Asp Tyr Val Ile Arg Val Gly Lys Pro Val Ile Ser Lys
        275                 280                 285

Lys Leu Asn Gln Trp Leu Lys Lys Thr Asp Ala Tyr Gln Ile Ile Val
    290                 295                 300

Gln Asn Asn Asp Gln Ile Asp Val Phe Pro Thr Pro His Ile Ser
305                 310                 315                 320

Tyr Glu Ile Ser Ala Asn Asp Phe Phe Arg Ser Leu Met Glu Pro
                325                 330                 335

Leu Val Glu Arg Lys Lys Trp Leu Gln Gln Trp Gln Ser Leu Glu Gln
            340                 345                 350

Gln Ala Arg Ile Glu Ile Ser Asp Tyr Leu Lys His Ala Thr Asp Glu
        355                 360                 365

Ala Ala Tyr Val Gly Ser Leu Ile Gln Lys Leu Thr Lys Glu Asp Thr
    370                 375                 380

Leu Phe Val Gly Asn Ser Met Pro Ile Arg Asp Val Asp Asn Leu Leu
385                 390                 395                 400

Phe Asp Ser Glu Ala Ser Val Tyr Ala Asn Arg Gly Ala Asn Gly Ile
```

```
            405                 410                 415
Asp Gly Val Val Ser Thr Ala Leu Gly Met Ala Ala His Lys Asn Val
            420                 425                 430

Thr Leu Leu Ile Gly Asp Leu Ser Phe Tyr His Asp Met Asn Gly Leu
            435                 440                 445

Leu Met Ala Lys Leu Asn Glu Leu His Ile Asn Ile Val Leu Val Asn
450                 455                 460

Asn Asn Gly Gly Gly Ile Phe Ser Tyr Leu Pro Gln Lys Arg Ser Ala
465                 470                 475                 480

Thr Lys Tyr Phe Glu Arg Leu Phe Gly Thr Pro Thr Gly Leu Asn Phe
            485                 490                 495

Glu Tyr Thr Ala Leu Leu Tyr Asp Phe Thr Phe Lys Arg Phe Asp Asn
            500                 505                 510

Leu Thr Asp Phe Lys Tyr Ala Glu Leu Ser Lys Met Gly Ser His Met
            515                 520                 525

Tyr Glu Val Ile Thr Asn Arg Asp Glu Asn Leu His Gln His Gln Asn
            530                 535                 540

Leu Tyr Gln Lys Leu Ser Glu Ile Val Asn Val Thr Leu
545                 550                 555

<210> SEQ ID NO 4
<211> LENGTH: 557
<212> TYPE: PRT
<213> ORGANISM: Staphylococcus epidermidis

<400> SEQUENCE: 4

Met Met Asn His Ser Glu Ala Leu Thr Glu Gln Val Phe Ser Phe Ala
1               5                   10                  15

Ser Glu Leu Tyr Ala Tyr Gly Val Arg Glu Val Val Ile Ser Pro Gly
            20                  25                  30

Ser Arg Ser Thr Pro Leu Ala Leu Ala Phe Glu Ala His Pro Asn Ile
        35                  40                  45

Lys Thr Trp Ile His Pro Asp Glu Arg Ser Ala Ala Phe Phe Ala Leu
    50                  55                  60

Gly Leu Ile Lys Gly Ser Glu Lys Pro Val Ala Ile Leu Cys Thr Ser
65                  70                  75                  80

Gly Thr Ala Ala Ala Asn Tyr Thr Pro Ala Ile Ala Glu Ser Gln Ile
            85                  90                  95

Ser Arg Leu Pro Leu Val Val Leu Thr Ser Asp Arg Pro His Glu Leu
            100                 105                 110

Arg Ser Val Gly Ala Pro Gln Ala Ile Asn Gln Val Asn Met Phe Ser
        115                 120                 125

Asn Tyr Val Asn Phe Gln Phe Asp Leu Pro Ile Ala Asp Gly Ser Glu
    130                 135                 140

His Thr Ile Asp Thr Ile Asn Tyr Gln Met Gln Ile Ala Ser Gln Tyr
145                 150                 155                 160

Leu Tyr Gly Pro His Arg Gly Pro Ile His Phe Asn Leu Pro Phe Arg
            165                 170                 175

Glu Pro Leu Thr Pro Asp Leu Asp Arg Val Asp Leu Leu Thr Ser Val
            180                 185                 190

Thr Lys Thr Leu Pro His Tyr Gln Lys Ser Ile Ser Val Asp Asp Ile
        195                 200                 205

Lys Asp Ile Leu Gln Glu Lys Asn Gly Leu Ile Ile Val Gly Asp Met
    210                 215                 220

Gln His Gln Ala Val Asp Gln Ile Leu Thr Tyr Ser Thr Ile Tyr Asp
```

```
              225                 230                 235                 240
Leu Pro Ile Leu Ala Asp Pro Leu Ser Gln Leu Arg Lys Glu Lys His
                245                 250                 255

Pro Asn Val Ile Thr Thr Tyr Asp Leu Leu Tyr Arg Ala Gly Leu Asn
            260                 265                 270

Leu Glu Val Asp Tyr Val Ile Arg Val Gly Lys Pro Val Ile Ser Lys
        275                 280                 285

Lys Leu Asn Gln Trp Leu Lys Lys Thr Asp Ala Tyr Gln Ile Ile Val
    290                 295                 300

Gln Asn Asn Asp Gln Ile Asp Val Phe Pro Thr Pro His Ile Ser
305                 310                 315                 320

Tyr Glu Ile Ser Ala Asn Asp Phe Phe Arg Ser Leu Met Glu Glu Pro
                325                 330                 335

Leu Val Glu Arg Lys Lys Trp Leu Gln Gln Trp Gln Ser Leu Glu Gln
            340                 345                 350

Gln Ala Arg Ile Glu Ile Ser Asp Tyr Leu Lys His Ala Thr Asp Glu
        355                 360                 365

Ala Ala Tyr Val Gly Ser Leu Ile Gln Lys Leu Thr Lys Glu Asp Thr
    370                 375                 380

Leu Phe Val Gly Asn Ser Met Pro Ile Arg Asp Val Asp Asn Leu Leu
385                 390                 395                 400

Phe Asp Ser Glu Ala Ser Val Tyr Ala Asn Arg Gly Ala Asn Gly Ile
                405                 410                 415

Asp Gly Val Val Ser Thr Ala Leu Gly Met Ala Ala His Lys Asn Val
            420                 425                 430

Ile Leu Leu Ile Gly Asp Leu Ser Phe Tyr His Asp Met Asn Gly Leu
        435                 440                 445

Leu Met Ala Lys Leu Asn Glu Leu His Ile Asn Ile Val Leu Val Asn
    450                 455                 460

Asn Asn Gly Gly Gly Ile Phe Ser Tyr Leu Pro Gln Lys Arg Ser Ala
465                 470                 475                 480

Thr Lys Tyr Phe Glu Arg Leu Phe Gly Thr Pro Thr Gly Leu Asn Phe
                485                 490                 495

Glu Tyr Thr Ala Leu Leu Tyr Asp Phe Thr Phe Lys Arg Phe Asp Asn
            500                 505                 510

Leu Thr Asp Phe Lys Tyr Ala Glu Leu Ser Lys Met Gly Ser His Met
        515                 520                 525

Tyr Glu Val Ile Thr Asn Arg Asp Glu Asn Leu His Gln His Gln Asn
    530                 535                 540

Leu Tyr Gln Lys Leu Ser Glu Ile Val Asn Val Thr Leu
545                 550                 555

<210> SEQ ID NO 5
<211> LENGTH: 1674
<212> TYPE: DNA
<213> ORGANISM: Staphylococcus epidermidis

<400> SEQUENCE: 5
atgatgaatc atagtgaagc tttaactgaa caagtatttt catttgcttc agagctttat     60
gcttatggtg taagagaagt agtaattagt ccaggttcac gttcaacacc attagcactt    120
gttttcgaag cacatccaaa tattaaaaca tggattcacc ctgatgagcg aagtgctgca    180
ttttttgctt taggtcttat taaaggtagc gaaaaacctg tagcaattct ttgtacatct    240
ggaacagccg ctgcgaacta cacacccgct atagctgaaa gtcaaattag tcgtttgcct    300
```

-continued

```
ctcgttgttt taacgagcga cagaccgcat gaactgcgca gtgtgggtgc acctcaagca      360
atcaatcagg taaatatgtt tagtaattat gtgaactttc aatttgattt gccgattgct      420
gatggaagtg aacatacaat tgatacaatt aattatcaaa tgcaaattgc aagtcaatat      480
ttatatggac cacaccgagg accgattcat tttaatttac catttagaga accactaaca      540
ccagatttag atcgtgtcga tttattaaca tctgtaacta aaacgttacc tcattatcag      600
aaatcgattt cggtagatga tataaaagac atattacaag aaaaaaatgg tctcatcatt      660
gtcggagata tgcaacacca agctgttgat caaatattaa cgtattcaac tatatatgat      720
ctgccaatct tagcagatcc ccttagtcag cttcgtaaag agaaacatcc taatgttata      780
accacttatg atttattgta tcgagcagga ttaaatttag aagtagacta tgtcatacgt      840
gtaggtaagc cagttatttc taaaaaatta aatcaatggt tgaagaaaac cgatgcgtat      900
caaattattg tgcagaataa tgatcaaatt gatgtatttc cgacaccacc tcatatatct      960
tatgagattt cagcaaatga tttttttccgt tcattaatgg aagaaccact tgttgaacga     1020
aaaaaatggt tacagcaatg gcaatcactt gaacaacaag cacgcattga aataagtgat     1080
tacttaaagc atgcgacaga tgaagcggca tatgtaggga gtttaattca aaaacttaca     1140
aaagaagata cattatttgt tggaaatagt atgccaatta gagatgtcga taatttactg     1200
tttgatagtg aggcatctgt atacgctaat cggggtgcca atggaataga cggagtagtt     1260
tcaactgcgc taggtatggc ggcacataag aatgtgacat tgcttattgg tgatttatct     1320 tttatcatg acatgaacgg tttattaatg gccaaattaa atgaacttca tattaacatt     1380
gtattagtta ataacaacgg aggaggtatc ttttcatatt tacctcaaaa acgatcggct     1440
acaaaatatt ttgagcgatt atttggaaca ccaacaggct aaactttga atatactgca     1500 ctgttatatg attttacatt taagcgcttt gataatttga ctgactttaa atatgctgaa     1560
ttatctaaaa tgggttctca catgtatgaa gttataacca atagagacga aaatttgcat     1620
caacaccaaa atttatatca gaaattgagt gagattgtta atgttacatt ataa           1674
```

POLYPEPTIDES FOR INDUCING A PROTECTIVE IMMUNE RESPONSE AGAINST *STAPHYLOCOCCUS EPIDERMIDIS*

CROSS-REFERENCE TO RELATED APPLICATIONS

This application claims the benefit of U.S. Provisional Application No. 60/897,150 filed Jan. 24, 2007, herein incorporated by reference.

REFERENCE TO SEQUENCE LISTING SUBMITTED ELECTRONICALLY

The sequence listing of the present application is submitted electronically via EFS-Web as an ASCII formatted sequence listing with a file name "MRLBIO22192USPCT_SEQLIST_11DEC.2009.TXT", created Dec. 11, 2009, and having a size of 20 KB. This sequence listing submitted via EFS-Web is part of the specification and is herein incorporated by reference in its entirety.

BACKGROUND OF THE INVENTION

The references cited throughout the present application are not admitted to be prior art to the claimed invention.

*Staphylococcus epidermidis* has emerged as pathogen, particularly in nosocomial and immune compromised patients. (Ziebuhr et al., *International Journal of Antimicrobial Agents* 28S:S14-S20, 2006.) Coagulase-negative staphylococci (CoNS), mainly *S. epidermidis*, are the most frequently isolated microorganism infection associated with foreign bodies used in diagnostic or therapeutic procedures. (Heilmann and Peters, Biology and Pathogenicity of *Staphylococcus epidermidis*, In: Gram Positive Pathogens, Eds. Fischetti et al., American Society for Microbiology, Washington D.C. 2000 and *The Staphylococci in Human Disease*, Crossley and Archer (eds.), Churchill Livingstone Inc. 1997.)

Nucleic acid from *S. epidermis* has been sequenced to obtain nucleic acid sequence information and make predictions concerning open reading frames and potential polypeptides. (Doucette-Stamm et al., U.S. Pat. No. 6,380,370 and Doucette-Stamm et al., U.S. Pat. No. 7,060,458.)

Techniques such as those involving display technology and sera from infected patients can be used in an effort to identify genes coding for potential antigens. (Meinke et al., International Publication No. WO 02/059148, Meinke et al., International Publication No. WO 04/087746.)

SUMMARY OF THE INVENTION

The present invention features polypeptides comprising an amino acid sequence structurally related to SEQ ID NO: 1 and uses of such polypeptides. SEQ ID NO: 1 is a truncated derivative of a full-length *S. epidermidis* polypeptide. The full-length naturally occurring polypeptide is referred to herein as full-length ORF1319e. A His-tagged derivative of SEQ ID NO: 1 was found to produce a protective immune response against *S. epidermidis*.

Reference to "protective" immunity or immune response indicates a detectable level of protection against *S. epidermidis* infection. Reference to "immunogen" indicates the ability to provide protective immunity.

Thus, a first aspect of the present invention describes a polypeptide immunogen comprising an amino acid sequence at least 85% identical to SEQ ID NO: 1, wherein the polypeptide does not have the amino acid sequence of SEQ ID NOs: 3 or 4. In an embodiment, the polypeptide does not contain an amino terminus provided by amino acids 1-93 of SEQ ID NO: 3.

Reference to comprising an amino acid sequence at least 85% identical to SEQ ID NO: 1 indicates that a SEQ ID NO: 1 related region is present and additional polypeptides regions may be present. In an embodiment, if additional regions are present, the polypeptide does not have an amino terminus provided by amino acids 1-93 of SEQ ID NO: 3.

Percent identity (also referred to as percent identical) to a reference sequence is determined by aligning the polypeptide sequence with the reference sequence and determining the number of identical amino acids in the corresponding regions. This number is divided by the total number of amino acids in the reference sequence (e.g., SEQ ID NO: 1) and then multiplied by 100 and rounded to the nearest whole number.

Another aspect of the present invention describes an immunogen comprising an amino acid sequence that provides protective immunity against *S. epidermidis* and one or more additional regions or moieties covalently joined to the sequence at the carboxyl terminus or amino terminus, wherein each region or moiety is independently selected from a region or moiety having at least one of the following properties: enhances the immune response, facilitates D purification, or facilitates polypeptide stability.

Reference to "additional region or moiety" indicates a region or moiety different from a ORF1319e region. The additional region or moiety can be, for example, an additional polypeptide region or a non-peptide region.

Another aspect of the present invention describes a composition able to induce protective immunity against *S. epidermidis* in a patient. The composition comprises a pharmaceutically acceptable carrier and an immunologically effective amount of an immunogen that provides protective immunity against *S. epidermidis*.

An immunologically effective amount is an amount sufficient to provide protective immunity against *S. epidermidis* infection. The amount should be sufficient to significantly prevent the likelihood or severity of a *S. epidermidis* infection.

Another aspect of the present invention describes a nucleic acid comprising a recombinant gene encoding a polypeptide that provides protective immunity against *S. epidermidis*. A recombinant gene contains recombinant nucleic acid encoding a polypeptide along with regulatory elements for proper transcription and processing (which may include translational and post translational elements). The recombinant gene can exist independent of a host genome or can be part of a host genome.

A recombinant nucleic acid is nucleic acid that by virtue of its sequence and/or form does not occur in nature. Examples of recombinant nucleic acid include purified nucleic acid, two or more nucleic acid regions combined together that provides a different nucleic acid than found in nature, and the absence of one or more nucleic acid regions (e.g., upstream or downstream regions) that are naturally associated with each other.

Another aspect of the present invention describes a recombinant cell. The cell comprises a recombinant gene encoding a polypeptide that provides protective immunity against *S. epidermidis*. Preferably, the cell is grown in vitro.

Another aspect of the present invention describes a method of making a polypeptide that provides protective immunity against *S. epidermidis*. The method involves growing a recombinant cell containing recombinant nucleic acid encoding the polypeptide and purifying the polypeptide.

Another aspect of the present invention describes a polypeptide that provides protective immunity against *S. epi-*

*dermidis* made by a process comprising the steps of growing a recombinant cell containing recombinant nucleic acid encoding the polypeptide in a host and purifying the polypeptide. Different host cells can be employed.

Another aspect of the present invention describes a method of inducing a protective immune response in a patient against *S. epidermidis*. The method comprises the step of administering to the patient an immunologically effective amount of an immunogen providing protective immunity against *S. epidermidis*.

Unless particular terms are mutually exclusive, reference to "or" indicates either or both possibilities. Occasionally phrases such as "and/or" are used to highlight either or both possibilities.

Reference to open-ended terms such as "comprises" allows for additional elements or steps. Occasionally phrases such as "one or more" are used with or without open-ended terms to highlight the possibility of additional elements or steps.

Unless explicitly stated reference to terms such as "a" or "an" is not limited to one. For example, "a cell" does not exclude "cells". Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

BRIEF DESCRIPTION OF THE DRAWINGS

FIG. 1 illustrates the amino acid sequence of SEQ ID NO: 2. SEQ ID NO: 2 is a His-Tag derivative of SEQ ID NO: 1. The SEQ ID NO: 1 region is shown in bold.

FIGS. 2A and 2B illustrate the full-length ORF1319e of SEQ ID NO: 3 (FIG. 2A) and the encoding nucleic acid (FIG. 2B, SEQ ID NO: 5). The SEQ ID NO: 1 region is shown in bold in FIG. 2A. The SEQ ID NO: 1 encoding region is shown in bold in FIG. 2B.

FIG. 3 illustrates the amino acid sequence of SEQ ID NO: 4.

DETAILED DESCRIPTION OF THE INVENTION

The ability of SEQ ID NO: 1 related polypeptides to provide protective immunity is illustrated in the Examples provided below using SEQ ID NO: 2. SEQ ID NO: 2 is a His-Tag derivative of SEQ ID NO: 1. The His-tag facilitates polypeptide purification and identification. FIG. 1 illustrates SEQ ID NO: 2, where the SEQ ID NO: 1 region is shown in bold.

SEQ ID NO: 1 is a derivative of the full length ORF1319e *S. epidermidis* polypeptide. SEQ ID NO: 1 contains amino acids 94-557 of a ORF1319e sequence (SEQ ID NO: 3). Amino acids 1-93 were predicted to contain a signal sequence. The full-length sequence of SEQ ID NO: 3 is 557 amino acids. FIGS. 2A and 2B illustrate SEQ ID NO: 3 and an encoding nucleic acid sequence, where the SEQ ID NO: 1 region is shown in bold.

ORF1319e Sequences

Examples of ORF1319e related sequences are provided in Gen-Bank Accession Nos. Q8CPQ5 and Q5HQC5. Gen-Bank Accession Nos. Q5HQC5 corresponds to SEQ ID NO: 3. Gen-Bank Accession Nos. Q5HQC5 references Gill et al., *J Bacteriol.* 187(7):2426-2438, 2005. Gen-Bank Accession Nos. Q8CPQ5 (SEQ ID NO: 4) differs from SEQ ID NO: 3 by having an alanine, instead of valine, in amino acid 42. Gen-Bank Accession Nos. Q8CPQ5 references Zhang et al., *Mol. Microbiol.* 49(6):1577-1593, 2003.

Other naturally occurring ORF1319e sequences can be identified based on the presence of a high degree of sequence similarity or contiguous amino acids compared to a known ORF1319e sequence. Contiguous amino acids provide characteristic tags. In different embodiments, a naturally occurring ORF1319e sequence is a sequence found in a *Staphylococcus* sp, preferably *S. epidermidis*, having at least 20, at least 30, or at least 50 contiguous amino acids as in SEQ ID NO: 1; and/or having at least 85% sequence similarity or identity with SEQ ID NO: 1.

Sequence similarity can be determined by different algorithms and techniques well known in the art. Generally, sequence similarity is determined by techniques aligning two sequences to obtain maximum amino acid identity, allowing for gaps, additions and substitutions in one of the sequences.

Sequence similarity can be determined, for example, using a local alignment tool utilizing the program lalign (developed by Huang and Miller, *Adv. Appl. Math.* 12:337-357, 1991, for the <<sim>> program). The options and environment variables are: –f # Penalty for the first residue a gap (–14 by default); –g # Penalty for each additional residue in a gap (–4 by default)-s str (SMATRIX) the filename of an alternative scoring matrix file. For protein sequences, PAM250 is used by default-w # (LINLEN) output line length for sequence alignments (60).

SEQ ID NO: 1 Related Polypeptides

Polypeptides structurally related to SEQ ID NO: 1 include polypeptides containing corresponding regions present in different *S. epidermidis* strains and derivatives of naturally occurring regions. SEQ ID NO: 1 related polypeptides contain an amino acid sequence at least 85% identical to SEQ ID NO: 1. Reference to "polypeptide" does not provide a minimum or maximum size limitation.

A polypeptide at least 85% identical to SEQ ID NO: 1 contains up to about 70 amino acid alterations from SEQ ID NO: 1. Each amino acid alteration is independently an amino acid substitution, deletion, or addition. The alterations can be within the SEQ ID NO: 1 region or added to the SEQ ID NO: 1 region. In different embodiments, the SEQ ID NO: 1 related polypeptide is at least 90%, at least 94%, or at least 99% identical to SEQ ID NO: 1; differs from SEQ ID NO: 1 by 0, 1, 2, 3, 4, 5, 6, 7, 8, 9, 10, 11, 12, 13, 14, 15, 16, 17, 18, 19, or 20 amino acid alterations; or consists essentially of SEQ ID NO: 1.

Reference to "consists essentially" of indicated amino acids indicates that the referred to amino acids are present and additional amino acids may be present. The additional amino acids can be at the carboxyl or amino terminus. In different embodiments 1, 2, 3, 4, 5, 6, 7, 8, 9, 10, 11, 12, 13, 14, 15, 16, 17, 18, 19, or 20 additional amino acids are present. A preferred additional amino acid is an amino terminus methionine.

Alterations can be made to SEQ ID NO: 1 to obtain derivatives that can induce protective immunity against *S. epidermidis*. Alterations can be performed, for example, to obtain a derivative retaining the ability to induce protective immunity against *S. epidermidis* or to obtain a derivative that in addition to providing protective immunity also has a region that can achieve a particular purpose.

Alterations can be made taking into account different ORF1319e sequences and known properties of amino acids. Generally, in substituting different amino acids to retain activity it is preferable to exchange amino acids having similar properties. Factors that can be taken into account for an amino acid substitution include amino acid size, charge, polarity, and hydrophobicity. The effect of different amino acid R-groups on amino acid properties are well known in the art. (See, for example, Ausubel, *Current Protocols in Molecular Biology*, John Wiley, 1987-2002, Appendix 1C.)

In exchanging amino acids to maintain activity, the replacement amino acid should have one or more similar properties such as approximately the same charge and/or size and/or polarity and/or hydrophobicity. For example, substituting valine for leucine, arginine for lysine, and asparagine for glutamine are good candidates for not causing a change in polypeptide functioning.

Alterations to achieve a particular purpose include those designed to facilitate production or efficacy of the polypeptide; or cloning of the encoded nucleic acid. Polypeptide production can be facilitated through the use of an initiation codon (e.g., coding for methionine) suitable for recombinant expression. The methionine may be later removed during cellular processing. Cloning can be facilitated by, for example, the introduction of restriction sites which can be accompanied by amino acid additions or changes.

Efficacy of a polypeptide to induce an immune response can be enhanced through epitope enhancement. Epitope enhancement can be performed using different techniques such as those involving alteration of anchor residues to improve peptide affinity for MHC molecules and those increasing affinity of the peptide-MHC complex for a T-cell receptor. (Berzofsky et al., *Nature Review* 1:209-219, 2001.)

Preferably, the polypeptide is a purified polypeptide. A "purified polypeptide" is present in an environment lacking one or more other polypeptides with which it is naturally associated and/or is represented by at least about 10% of the total protein present. In different embodiments, the purified polypeptide represents at least about 50%, at least about 75%, or at least about 95% of the total protein in a sample or preparation.

In an embodiment, the polypeptide is "substantially purified." A substantially purified polypeptide is present in an environment lacking all, or most, other polypeptides with which the polypeptide is naturally associated. For example, a substantially purified *S. epidermidis* polypeptide is present in an environment lacking all, or most, other *S. epidermidis* polypeptides. An environment can be, for example, a sample or preparation.

Reference to "purified" or "substantially purified" does not require a polypeptide to undergo any purification and may include, for example, a chemically synthesized polypeptide that has not been purified.

Polypeptide stability can be enhanced by modifying the polypeptide carboxyl or amino terminus. Examples of possible modifications include amino terminus protecting groups such as acetyl, propyl, succinyl, benzyl, benzyloxycarbonyl or t-butyloxycarbonyl; and carboxyl terminus protecting groups such as amide, methylamide, and ethylamide.

In an embodiment of the present invention the polypeptide immunogen is part of an immunogen containing one or more additional regions or moieties covalently joined to the polypeptide at the carboxyl terminus or amino terminus, where each region or moiety is independently selected from a region or moiety having at least one of the following properties: enhances the immune response, facilitates purification, or facilitates polypeptide stability. Polypeptide stability can be enhanced, for example, using groups such as polyethylene glycol that may be present on the amino or carboxyl terminus.

Polypeptide purification can be enhanced by adding a group to the carboxyl or amino terminus to facilitate purification. Examples of groups that can be used to facilitate purification include polypeptides providing affinity tags. Examples of affinity tags include a six-histidine tag, trpE, glutathione and maltose-binding protein.

The ability of a polypeptide to produce an immune response can be enhanced using groups that generally enhance an immune response. Examples of groups that can be joined to a polypeptide to enhance an immune response against the polypeptide include cytokines such as IL-2. (Buchan et al., 2000. *Molecular Immunology* 37:545-552.)

Polypeptide Production

Polypeptides can be produced using standard techniques including those involving chemical synthesis and those involving purification from a cell producing the polypeptide. Techniques for chemical synthesis of polypeptides are well known in the art. (See e.g., Vincent, *Peptide and Protein Drug Delivery*, New York, N.Y., Decker, 1990.) Techniques for recombinant polypeptide production and purification are also well known in the art. (See for example, Ausubel, *Current Protocols in Molecular Biology*, John Wiley, 1987-2002.)

Obtaining polypeptides from a cell is facilitated using recombinant nucleic acid techniques to produce the polypeptide. Recombinant nucleic acid techniques for producing a polypeptide involve introducing, or producing, a recombinant gene encoding the polypeptide in a cell and expressing the polypeptide.

A recombinant gene contains nucleic acid encoding a polypeptide along with regulatory elements for polypeptide expression. The recombinant gene can be present in a cellular genome or can be part of an expression vector.

The regulatory elements that may be present as part of a recombinant gene include those naturally associated with the polypeptide encoding sequence and exogenous regulatory elements not naturally associated with the polypeptide encoding sequence. Exogenous regulatory elements such as an exogenous promoter can be useful for expressing a recombinant gene in a particular host or increasing the level of expression. Generally, the regulatory elements that are present in a recombinant gene include a transcriptional promoter, a ribosome binding site, a terminator, and an optionally present operator. A preferred element for processing in eukaryotic cells is a polyadenylation signal.

Expression of a recombinant gene in a cell is facilitated through the use of an expression vector. Preferably, an expression vector in addition to a recombinant gene also contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses.

Due to the degeneracy of the genetic code, a large number of different encoding nucleic acid sequences can be used to code for a particular polypeptide. The degeneracy of the genetic code arises because almost all amino acids are encoded by different combinations of nucleotide triplets or "codons". Amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Suitable cells for recombinant nucleic acid expression of SEQ ID NO: 1 related polypeptides are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *pseudomonas* genus such as *Ps. Fluorescens*. Examples of eukaryotic cells include mammalian cells; insect cells; yeast cells such as members of the *Saccharomyces* genus (e.g., *S. cerevisiae*), members of the *Pichia* genus (e.g., *P. pastoris*), members of the *Hansenula* genus (e.g., *H. polymorpha*), members of the *Kluyveromyces* genus (e.g., *K. lactis* or *K. fragilis*) and members of the *Schizosaccharomyces* genus (e.g., *S. pombe*).

Techniques for recombinant gene production, introduction into a cell, and recombinant gene expression are well known in the art. Examples of such techniques are provided in references such as Ausubel, *Current Protocols in Molecular Biology*, John Wiley, 1987-2002, and Sambrook et al., *Molecular Cloning, A Laboratory Manual*, 2$^{nd}$ Edition, Cold Spring Harbor Laboratory Press, 1989.

If desired, expression in a particular host can be enhanced through codon optimization. Codon optimization includes use of more preferred codons. Techniques for codon optimization in different hosts are well known in the art.

SEQ ID NO: 1 related polypeptides may contain post translational modifications, for example, N-linked glycosylation, O-linked glycosylation, or acetylation. Reference to "polypeptide" or an "amino acid" sequence of a polypeptide includes polypeptides containing one or more amino acids having a structure of a post-translational modification from a host cell, such as a yeast host.

Post translational modifications can be produced chemically or by making use of suitable hosts. For example, in *S. cerevisiae* the nature of the penultimate amino acid appears to determine whether the N-terminal methionine is removed. Furthermore, the nature of the penultimate amino acid also determines whether the N-terminal amino acid is N$^{\alpha}$-acetylated (Huang et al., *Biochemistry* 26: 8242-8246, 1987). Another example includes a polypeptide targeted for secretion due to the presence of a secretory leader (e.g., signal peptide), where the protein is modified by N-linked or O-linked glycosylation. (Kukuruzinska et al., *Ann. Rev. Biochem.* 56:915-944, 1987.)

Adjuvants

Adjuvants are substances that can assist an immunogen in producing an immune response. Adjuvants can function by different mechanisms such as one or more of the following: increasing the antigen biologic or immunologic half-life; improving antigen delivery to antigen-presenting cells; improving antigen processing and presentation by antigen-presenting cells; and inducing production of immunomodulatory cytokines. (Vogel, *Clinical Infectious Diseases* 30(suppl. 3):S266-270, 2000.) In an embodiment, an adjuvant is used.

A variety of different types of adjuvants can be employed to assist in the production of an immune response. Examples of particular adjuvants include aluminum hydroxide, aluminum phosphate, or other salts of aluminum, calcium phosphate, DNA CpG motifs, monophosphoryl lipid A, cholera toxin, *E. coli* heat-labile toxin, pertussis toxin, muramyl dipeptide, Freund's incomplete adjuvant, MF59, SAF, immunostimulatory complexes, liposomes, biodegradable microspheres, saponins, nonionic block copolymers, muramyl peptide analogues, polyphosphazene, synthetic polynucleotides, IFN-γ, IL-2, IL-12, and ISCOMS. (Vogel *Clinical Infectious Diseases* 30(suppl 3):S266-270, 2000, Klein et al., *Journal of Pharmaceutical Sciences* 89:311-321, 2000, Rimmelzwaan et al., *Vaccine* 19:1180-1187, 2001, Kersten *Vaccine* 21:915-920, 2003, O'Hagen *Curr. Drug Target Infect. Disord.*, 1:273-286, 2001.)

Patients for Inducing Protective Immunity

A "patient" refers to a mammal capable of being infected with *S. epidermidis*. A patient can be treated prophylactically or therapeutically. Prophylactic treatment provides sufficient protective immunity to reduce the likelihood, or severity, of a *S. epidermidis* infection. Therapeutic treatment can be performed to reduce the severity of a *S. epidermidis* infection.

Prophylactic treatment can be performed using a vaccine containing an immunogen described herein. Such treatment is preferably performed on a human. Vaccines can be administered to the general population or to those persons at an increased risk of *S. epidermidis* infection.

Persons with an increased risk of *S. epidermidis* infection include health care workers; hospital patients; patients with a weakened immune system; patients undergoing surgery; patients receiving foreign body implants, such a catheter or a vascular device; patients facing therapy leading to a weakened immunity; patients under diagnostic procedures involving foreign bodies, and persons in professions having an increased risk of burn or wound injury.

Foreign bodies used in diagnostic or therapeutic procedures include indwelling catheters or implanted polymer devices. Examples of foreign bodies associated *S. epidermis* infections include stepticemia/endocarditis (e.g., intravascular catheters, vascular prostheses, pacemaker leads, defibrillator systems, prosthetic heart valves, and left ventricular assist devices); peritonitis (e.g., ventriculo-peritoneal cerebrospinal fluid (CSF) shunts and continuous ambulatory peritoneal dialysis catheter systems); ventriculitis (e.g., internal and external CSF shunts); and chronic polymer-associated syndromes (e.g., prosthetic joint (hip) loosening, fibrous capsular contracture syndrome after mammary argumentation with silicone prosthesis and late-onset endophtalmisis after implantation of artificial intraocular lenses following cataract surgery). (Heilmann and Peters, Biology and Pathogenicity of *Staphylococcus epidermidis*, In: Gram Positive Pathogens, Eds. Fischetti et al., American Society for Microbiology, Washington D.C. 2000.)

Non-human patients that can be infected with *S. epidermidis* include cows, pigs, sheep, goats, rabbits, horses, dogs, cats and mice. Treatment of non-human patients is useful in protecting pets and livestock, and in evaluating the efficacy of a particular treatment.

In an embodiment, a patient is treated prophylactically in conjunction with a therapeutic or medical procedure involving a foreign body. In additional embodiments, the patient is immunized at about 1 month, about 2 month or about 2-6 months prior to the procedure.

Combination Vaccines

SEQ ID NO: 1 related polypeptides can be used alone, or in combination with other immunogens, to induce an immune response. Additional immunogens that may be present include one or more additional *S. epidermidis* immunogens, one or more immunogens targeting one or more other *Staphylococcus* organisms such as *S. aureus, S. haemolyticus, S. warneri*, or *S. lugunensi*, and/or one or more immunogens targeting other infections organisms.

Examples of one or more additional immunogens include ORF0657n related polypeptides (Anderson et al., International Publication No. WO 05/009379); ORF0657/ORF0190 hybrid polypeptides (Anderson et al., International Publication No. WO 05/009378); sai-1 related polypeptides (Anderson et al., International Publication No. WO 05/79315); ORF0594 related polypeptides (Anderson et al., International Publication No. WO 05/086663); ORF0826 related polypeptides (Anderson et al., International Publication No. WO 05/115113); PBP4 related polypeptides (Anderson et al., International Publication No. WO 06/033918); AhpC related polypeptides and AhpC-AhpF compositions (Kelly et al. International Publication No. WO 06/078680); *S. aureus* type 5 and type 8 capsular polysaccharides (Shinefield et al., *N. Eng. J. Med.* 346:491-496, 2002); collagen adhesin, fibrinogen binding proteins, and clumping factor (Mamo et al., *FEMS Immunology and Medical Microbiology* 10:47-54, 1994, Nilsson et al., *J. Clin. Invest.* 101:2640-2649, 1998, Josefsson et al., *The Journal of Infectious Diseases* 184:1572-1580, 2001) and polysaccharide intercellular adhesin and fragments thereof (Joyce et al., *Carbohydrate Research* 338:903-922, 2003).

Administration

Immunogens can be formulated and administered to a patient using the guidance provided herein along with techniques well known in the art. Guidelines for pharmaceutical administration in general are provided in, for example, Vaccines Eds. Plotkin and Orenstein, W.B. Sanders Company, 1999; *Remington's Pharmaceutical Sciences* 20$^{th}$ Edition, Ed. Gennaro, Mack Publishing, 2000; and *Modern Pharmaceutics* 2$^{nd}$ Edition, Eds. Banker and Rhodes, Marcel Dekker, Inc., 1990.

Pharmaceutically acceptable carriers facilitate storage and administration of an immunogen to a patient. Pharmaceutically acceptable carriers may contain different components such as a buffer, sterile water for injection, normal saline or phosphate buffered saline, sucrose, histidine, salts and polysorbate.

Immunogens can be administered by different routes such as subcutaneous, intramuscular, or mucosal. Subcutaneous and intramuscular administration can be performed using, for example, needles or jet-injectors.

Suitable dosing regimens are preferably determined taking into account factors well known in the art including age, weight, sex and medical condition of the patient; the route of administration; the desired effect; and the particular compound employed. The immunogen can be used in multi-dose vaccine formats. It is expected that a dose would consist of the range of 1.0 µg to 1.0 mg total polypeptide. In different embodiments the range is from 5.0 µg to 500 µg, 0.01 mg to 1.0 mg and 0.1 mg to 1.0 mg.

The timing of doses depends upon factors well known in the art. After the initial administration one or more booster doses may subsequently be administered to maintain or boost antibody titers. An example of a dosing regime would be day 1, 1 month, a third dose at either 4, 6 or 12 months, and additional booster doses at distant times as needed.

Generation of Antibodies

A SEQ ID NO: 1 related polypeptide can be used to generate antibodies and antibody fragments binding to the polypeptide or to *S. epidermidis*. Such antibodies and antibody fragments have different uses including use in polypeptide purification, *S. epidermidis* identification, or in therapeutic or prophylactic treatment against *S. epidermidis* infection.

Antibodies can be polyclonal or monoclonal. Techniques for producing and using antibodies, including human antibodies, are well known in the art. (Ausubel, *Current Protocols in Molecular Biology*, John Wiley, 1987-2002, Harlow et al., *Antibodies, A Laboratory Manual*, Cold Spring Harbor Laboratory, 1988, Kohler et al., *Nature* 256:495-497, 1975, Azzazy et al., *Clinical Biochemistry* 35:425-445, 2002, Berger et al., *Am. J. Med. Sci.* 324(1):14-40, 2002.)

Proper glycosylation can be important for antibody function. (Yoo et al., *Journal of Immunological Methods* 261:1-20, 2002, Li et al., *Nature Biotechnology* 24(2):210-215, 2006.) Naturally occurring antibodies contain at least one N-linked carbohydrate attached to a heavy chain. (Yoo et al., *Journal of Immunological Methods* 261:1-20, 2002.) Additional N-linked carbohydrates and O-linked carbohydrates may be present and may be important for antibody function. (Id.)

Different types of host cells can be used to provide for efficient post-translational modifications including mammalian host cells and non-mammalian cells. Examples of mammalian host cells include Chinese hamster ovary (Cho), HeLa, C6, PC12, and myeloma cells. (Yoo et al., *Journal of Immunological Methods* 261:1-20, 2002, Persic et al., *Gene* 187:9-18, 1997.) Non-mammalian cells can be modified to replicate human glycosylation. (Li et al., *Nature Biotechnology* 24(2):210-215, 2006.) Glycoenginnered *Pichia pastoris* is an example of such a modified non-mammalian cell. (Li et al., *Nature Biotechnology* 24(2):210-215, 2006.)

Nucleic Acid Vaccine

Nucleic acid encoding a SEQ ID NO: 1 related polypeptide can be introduced into a patient using vectors suitable for therapeutic administration. Suitable vectors can deliver nucleic acid into a target cell without causing an unacceptable side effect. Examples of vectors that can be employed include plasmid vectors and viral based vectors. (Barouch *J. Pathol.* 208:283-289, 2006, Emini et al., International Publication No. WO 03/031588.)

Cellular expression is achieved using a gene expression cassette encoding a desired polypeptide. The gene expression cassette contains regulatory elements for producing and processing a sufficient amount of nucleic acid inside a target cell to achieve a beneficial effect.

Examples of viral vectors include first and second generation adenovectors, helper dependent adenovectors, adeno-associated viral vectors, retroviral vectors, alpha virus vectors, Venezuelan Equine Encephalitis virus vector, and plasmid vectors. (Hitt, et al., *Advances in Pharmacology* 40:137-206, 1997, Johnston et al., U.S. Pat. No. 6,156,588, Johnston et al., International Publication No. WO 95/32733, Barouch *J. Pathol.* 208:283-289, 2006, Emini et al., International Publication No. WO 03/031588.)

Adenovectors can be based on different adenovirus serotypes such as those found in humans or animals. Examples of animal adenoviruses include bovine, porcine, chimpanzee, murine, canine, and avian (CELO). (Emini et al., International Publication No. WO 03/031588, Colloca et al., International Publication No. WO 05/071093.) Human adenovirus include Group B, C, D, or E serotypes such as type 2 ("Ad2"), 4 ("Ad4"), 5 ("Ad5"), 6 ("Ad6"), 24 ("Ad24"), 26 ("Ad26"), 34 ("Ad34") and 35 ("Ad35").

Nucleic acid vaccines can be administered using different techniques and dosing regimes. (Emini et al., International Publication No. WO 03/031588.) For example, the vaccine can be administered intramuscular by injection with or without one or more electric pulses. Electric mediated transfer can assist genetic immunization by stimulating both humoral and cellular immune responses. Dosing regimes include prime-boost and heterologous prime-boost approaches. (Emini et al., International Publication No. WO 03/031588.)

EXAMPLES

Examples are provided below further illustrating different features of the present invention. The examples also illustrate useful methodology for practicing the invention. These examples do not limit the claimed invention.

Example 1

Protective Immunogen Production, Purification, and Formulation

SEQ ID NO: 2 was used in the examples described below to illustrate the ability of SEQ ID NO: 1 related polypeptides to provide protective immunity. SEQ ID NO: 2 is a His-tagged derivative of SEQ ID NO: 1.

ORF1319e Cloning and Expression and Modification

An ORF1319e DNA sequence was translated using Vector NTI software and the resulting 557 amino acid sequence was analyzed. PCR primers were designed to amplify the gene starting at aa 94 and ending prior to the stop codon at the terminal L residue. These PCR primers also had an additional HIS tag located on the forward primer to aid purification.

The protein was designed to be expressed from the pET-Blue-1 vector with the amino terminal His residues encoded via the insert and the stop codon encoded by the vector. In addition, a glycine residue was added to the protein after the methionine initiator. The resulting amplified (1419 bp) nucleic acid encoded the 473 (including start codon) amino acid sequence of SEQ ID NO: 2.

PCR amplified sequences were ligated into the pETBlue-1 vector (Novagen) directly using TA cloning. The vector was introduced into E. coli Novablue (Novagen) by heat shock. Colonies were selected, grown in LB with 100 μg/mL ampicillin, DNA minipreps were made (Qiagen), and insert integrity determined by restriction digestion and PCR. Minipreps with correct insert size were sequenced. A clone was selected containing no DNA changes from the desired sequence.

E. coli Tuner™ (DE3) pLacI (Novagen) were transformed and grown on LB plates containing ampicillin (100 ug/ml); 3 colonies were selected for expression testing. Liquid LB (ampicillin) cultures were incubated at 37° C., 250 rpm until the $A_{600}$ was between 0.6 and 1.0 and then induced by the addition of IPTG to final concentrations of 0.4 mM followed by three hours further incubation. Cultures (1.5 ml) were harvested by centrifugation at 14000 rpm for 1 minute at 4° C. Cells were resuspended in 300 μl lysis buffer (Bug Buster, with protease inhibitors, Novagen) and sonicated for 15 seconds for 3 times. An equal volume of loading buffer (supplemented with β-mecapto ethanol to 2% final volume) was added prior to heating the samples at 90° C. for 5 minutes. Extracts were run on Novex 4-20% Tris-Glycine gels and assayed for protein (Coomassie Blue stained) and blotted onto nitrocellulose and probed with anti-HIS6 antibodies (Zymedd).

SEQ ID NO: 2 Purification

Frozen recombinant E. coli cell paste was thawed and resuspended in two volumes of Lysis Buffer (50 mM sodium phosphate, pH 7.4, 0.5 M NaCl, 2 mM magnesium chloride, 10 mM imidazole, 0.1% Tween-80, Benzonase (EM #1.01697.0002) at 250 Units/mL, and protease inhibitor cocktail (Complete™, EDTA-Free, Roche #1873580)-one tablet per 50 ml. A lysate was prepared with a microfluidizer. The lysate was clarified by centrifugation at 10,000×g for 45 minutes at 4° C. The supernatant was discarded and the pellet, containing inclusion bodies, was washed 5 times with Wash Buffer (50 mM sodium phosphate, pH 7.4, 0.5 M NaCl, 2 mM magnesium chloride, 10 mM imidazole, and 0.1% Tween-80). The washed inclusion bodies were dissolved in 8 M Guanidine HCl+1 mM EDTA, and the solution was clarified by centrifugation at 10,000×g for one hour at 4° C. The supernatant was fractionated by size-exclusion chromatography using a Sephacryl S-300 26/60 column at a flow rate of 1 ml/min. The running buffer was 8 M Gd—HCl+1 mM EDTA. Peak SEC fractions were pooled and dialyzed into 8 M Urea. The urea-soluble product was sterile-filtered and adsorbed to aluminum hydroxyphosphate adjuvant at a final concentration of 0.2 mg/ml. Residual urea was removed by extensive washing of the alum-bound product with saline (multiple rounds of centrifugation and resuspension).

Example 2

Rat Indwelling Catheter Model (Multiple Immunizations)

SEQ ID NO: 2 and a rat indwelling catheter model was used to assess whether active immunization using SEQ ID NO: 1 related polypeptides can inhibit staphylococcal infection of implanted devices. A vaccine containing SEQ ID NO: 2 was obtained as described in Example 1.

Rats were purchased at 3-4 wks and immunized on day 0, 14 and 21 either IP with immunogen on aluminium hydroxide phosphate ("AHP") (Klein et al., *Journal of Pharmaceutical Sciences* 89:311-321, 2000), or mock immunized with adjuvant alone. On day 35 the animals had surgery to place an indwelling catheter in the jugular vein. The animals were rested for approximately 10 days after surgery, at which time a sub-lethal challenge of *S. epidermidis* strain RP62A was given IV (5-7×$10^9$ CFU). The rats were sacrificed 24 hours post challenge, and the catheters removed.

The presence of bacteria on the catheters was assessed by culturing the entire catheter on mannitol salt agar plates. If any sign of outgrowth was observed on the plate the catheter was scored as culture positive (Table 1). Sham immunized animals have >80% of the catheters colonized. For an immunogen to be considered protective <50% of the catheters are colonized by the challenge strain.

TABLE 1

Active Immunization Experiments using a Rat Indwelling Catheter Model

| Vaccine | # Infected Catheters (24 hr) | % Infected Catheters (24 hr) |
|---|---|---|
| AHP Control | 10/10 | 100 |
| SEQ ID NO: 2-AHP | 0/10 | 0 |

Example 3

Rat Indwelling Catheter Model (Single Immunizations)

To assess whether active immunization against staphylococcal vaccine candidates can prevent staphylococcal infection of implanted devices after a single dose, a rat indwelling catheter model was used. This time cannulated rats (6 weeks) were immunized with a single dose (20 μg) of SEQ ID NO: 2 on AHP (IP or IM) or a mock vaccine of BSA on AHP (20 μg, IP), and challenged on day 15 with *S. epidermidis* RP62A ($7.0 \times 10^9$ CFU/rat). 100% clearance of catheters was observed for the SEQ ID NO: 2 vaccinated animals (Table 2).

TABLE 2

Active Immunization Experiments using a Rat Indwelling Catheter Model

| Vaccine | Immune titer (Geomean) | # Infected Catheters (24 hr) | % Infected Catheters (24 hr) |
|---|---|---|---|
| BSA-MAA Control | 400 | 4/4 | 100 |
| SEQ ID NO: 2-AHP IP | 144,815 | 0/4 | 0 |
| SEQ ID NO: 2-AHP IM | 204,800 | 0/4 | 0 |

Example 4

Antibody Dependent Response

To confirm that clearance of bacteria from the indwelling catheters was antibody dependent, and not a result of potential occult stimulation of the innate immune system, an experiment was done in which cannulated rats (6 weeks) were immunized a single time with SEQ ID NO: 2-AHP or BSA-AHP, (20 μg, IP), or AHP alone (IP). Half of the rats were sacrificed each on days 5 or 14. At day 5 the active immune system could not be expected to produce antibody, whereas the innate immune system could be potentially stimulated. At day 14, the active immune system could be stimulated, and specific antibodies produced.

None of the catheters from the SEQ ID NO: 2 immunized animals were negative on day 5, whereas, half of the catheters from the SEQ ID NO: 2 immunized animals were negative on day 14 (see Table 3).

TABLE 3

Infected Catheters at Day 5 and Day 14

| Vaccine | # Infected Catheters (% Infected Catheters) Day 5 | # Infected Catheters (% Infected Catheters) Day 14 |
|---|---|---|
| SEQ ID NO: 2-AHP | 4/4 (100%) | 2/4 (50%) |
| BSA-AHP | 2/2 (100%) | 2/2 (100%) |
| AHP | 4/4 (100%) | 4/4 (100%) |

Other embodiments are within the following claims. While several embodiments have been shown and described, various modifications may be made without departing from the spirit and scope of the present invention.

What is claimed is:

1. A purified polypeptide immunogen comprising an amino acid sequence at least 99% identical to SEQ ID NO: 1, wherein said polypeptide provides protective immunity against *S. epidermidis* and the polypeptide does not comprise the amino acid sequence provided by SEQ ID NOs: 3 or 4.

2. The polypeptide of claim 1, wherein said polypeptide consists essentially of SEQ ID NO: 1.

3. The polypeptide of claim 2, wherein said polypeptide consists of the an amino acid sequence of SEQ ID NO: 1 or methionine-SEQ ID NO: 1.

4. A composition able to induce a protective immune response in a patient comprising an immunologically effective amount of the immunogen of claim 1 and a pharmaceutically acceptable carrier.

5. The composition of claim 4, wherein said composition further comprises an adjuvant.

* * * * *